United States Patent [19]
Haedt

[11] Patent Number: 5,611,782
[45] Date of Patent: Mar. 18, 1997

[54] METHOD OF DELIVERING A BLOOD SAMPLE TO AN EVACUATED RECEPTACLE

[75] Inventor: Lori E. Haedt, Marietta, Ga.

[73] Assignee: Becton, Dickinson and Company, Franklin Lakes, N.J.

[21] Appl. No.: 511,813

[22] Filed: Aug. 7, 1995

Related U.S. Application Data

[63] Continuation-in-part of Ser. No. 276,390, Jul. 18, 1994, Pat. No. 5,439,450.

[51] Int. Cl.$^6$ ................................................ A61M 5/32
[52] U.S. Cl. ................................ 604/198; 128/760
[58] Field of Search .................... 128/760, 763–766, 128/770; 604/192, 196–199

[56] References Cited

U.S. PATENT DOCUMENTS

| | | | |
|---|---|---|---|
| 4,874,383 | 10/1989 | McNaughton | 604/198 |
| 5,147,303 | 9/1992 | Martin | 604/198 |
| 5,169,392 | 12/1992 | Ranford et al. | 604/198 |
| 5,242,401 | 9/1993 | Colsky | 604/198 |
| 5,312,370 | 5/1994 | Talonn | 604/198 |

*Primary Examiner*—Max Hindenburg
*Attorney, Agent, or Firm*—John L. Voellmicke

[57] ABSTRACT

A method of delivering blood to an evacuated receptacle having a pierceable stopper and a cavity at a subatmospheric pressure, comprising the steps of:

a) providing a syringe comprising a barrel having an open proximal end, a distal end and a chamber, a needle cannula having a sharp distal end and a lumen therethrough connected to the distal end, a shield having an open distal end slidably mounted over the barrel for telescoping movement from a proximal position where the needle cannula projects through the open distal end of the shield to a distal position where the shield surround the needle cannula, a piston inside the barrel;

b) providing a catheter having a distal end and a passageway therethrough and a housing having a port in fluid communication with the passageway, a pierceable septum sealing the port;

c) placing the distal end of the catheter in a blood vessel;

d) piercing the pierceable septum with the needle and drawing blood from the vessel through the catheter, and into the chamber by manipulating the piston;

e) withdrawing the needle from the vessel;

f) moving the shield to the distal position;

g) inserting an evacuated receptacle into the shield until the sharp distal end of the needle cannula pierces the stopper and enters the cavity; and h) allowing blood to flow form the syringe chamber through the lumen into the cavity of the receptacle.

20 Claims, 11 Drawing Sheets

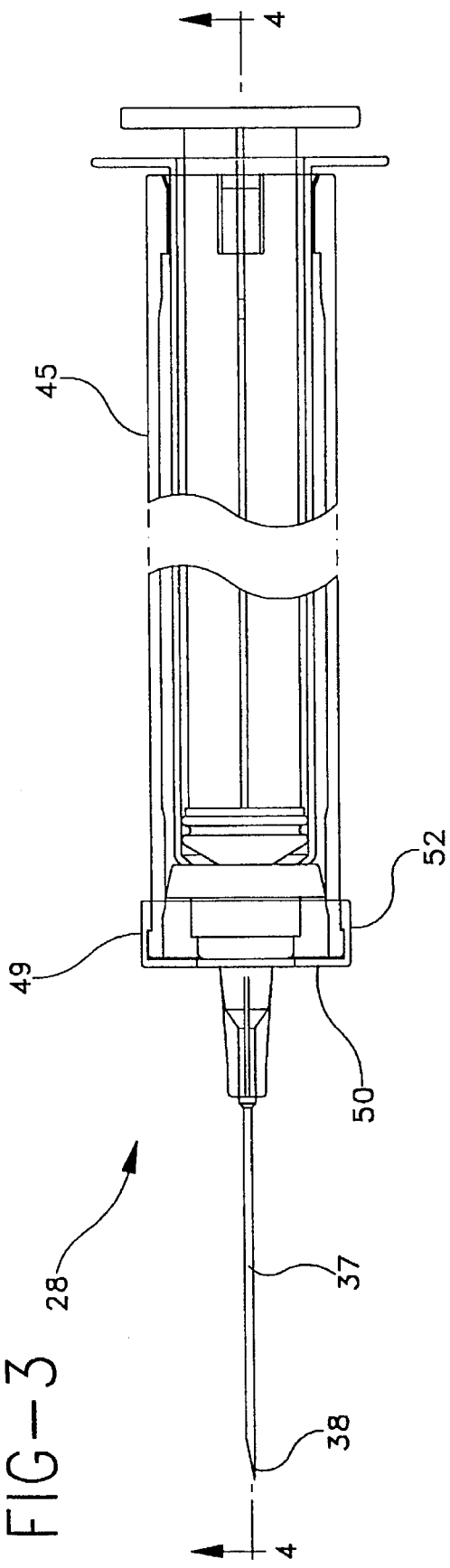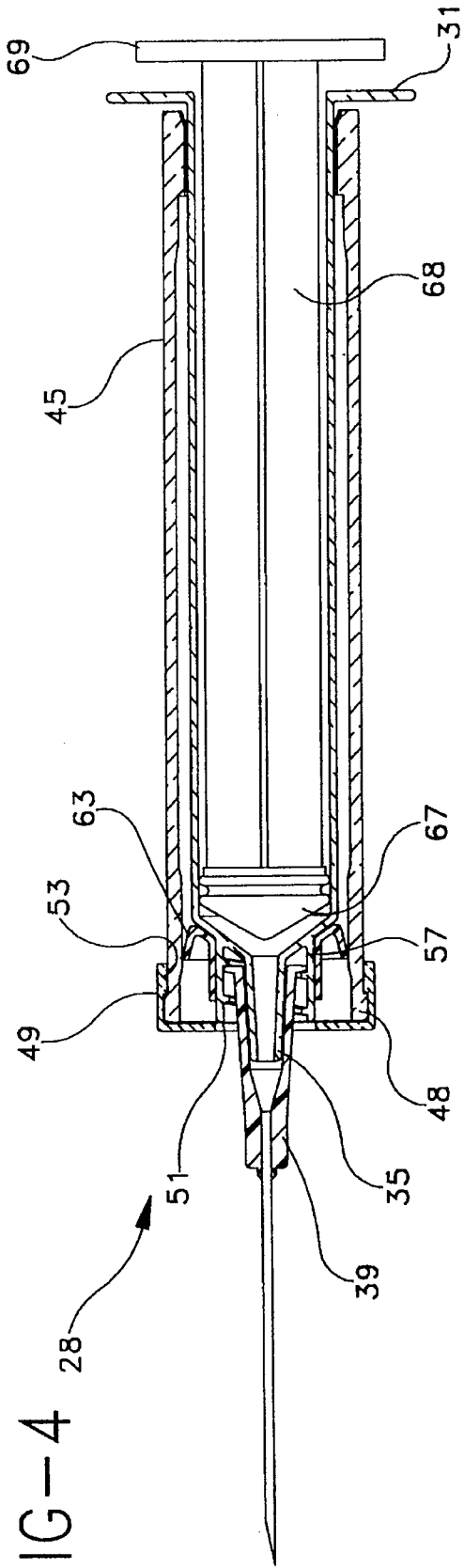

5,611,782

METHOD OF DELIVERING A BLOOD SAMPLE TO AN EVACUATED RECEPTACLE

This patent application is a continuation-in-part of U.S. patent application Ser. No. 08/276,390 filed on Jul. 18, 1994, U.S. Pat. No. 5,439,450.

FIELD OF THE INVENTION.

The subject invention relates to shielded safety syringes and a method of using such syringes for delivering a blood sample to an evacuated receptacle.

DESCRIPTION OF RELATED INFORMATION.

The most common method of withdrawing blood from a mammalian blood vessel, such as a vein or artery of a patient, is by piercing the blood vessel with one end of a double-ended needle cannula. The sharp end of the needle cannula which has not pierced the blood vessel is caused to pierce the pierceable stopper of an evacuated receptacle. When fluid communication is established between the evacuated receptacle and the blood vessel, blood will flow into the cavity of the evacuated receptacle which is initially at a subatmospheric pressure. Also, hypodermic syringes are used to withdraw blood from a vein or artery of a patient. A hypodermic syringe is preferred for withdrawing blood when the patient has weak veins that may collapse under the forces associated with withdrawing the blood directly into an evacuated receptacle. Also, the syringe is in a convenient blood collection device because the collected blood can be easily distributed to several different receptacles or test slides for various diagnostic procedures.

Blood is transferred from a hypodermic syringe to an evacuated receptacle by piercing the pierceable stopper of the receptacle with the needle on the blood filled syringe, and allowing the pressure differential between the evacuated receptacle and the atmosphere to drive the syringe piston and the blood into the receptacle. This method has a drawback in that the technician or medical professional delivering the blood sample to the evacuated receptacle must be careful not to stick herself with the sharpened needle cannula on the syringe which has previously been in the patient's vein. Such a stick could transfer a disease from the patient to the medical technician.

SUMMARY OF THE INVENTION

The present invention includes a method of delivering a blood sample to an evacuated receptacle having a closed end, an open end, a cylindrical side wall therebetween defining a cavity and a pierceable stopper occluding the open end of the receptacle. The cavity is at a subatmospheric pressure. The steps of the method comprise:

a) providing a syringe assembly comprising a syringe barrel having an open proximal end, a distal end and a side wall therebetween defining a chamber for retaining fluid, a needle cannula having a sharp distal end and a lumen therethrough connected to the distal end of the syringe barrel so that the lumen is in fluid communication with the chamber, a cylindrical safety shield having an open distal end and an open proximal end and a cap removably connected to the distal end of the safety shield, the cap including an end wall having an aperture smaller than the inside diameter of the open distal end of the shield and smaller than the outside diameter of the receptive stopper for limiting access to the open distal end of the shield, the safety shield is slidably mounted over the syringe barrel for telescoping movement from a proximal position where the needle cannula projects through the aperture of the cap to a distal position where the safety shield surrounds the needle cannula, a piston is in fluid-tight slidable engagement inside the barrel and connected to a rigid elongate plunger rod which extends proximally through the open end of the barrel;

b) piercing a mammalian blood vessel with the sharp distal end of the needle and drawing blood from the blood vessel into the chamber of the syringe barrel by manipulating the plunger rod;

c) withdrawing the needle cannula from the blood vessel;

d) moving the safety shield to the distal needle protecting position;

e) removing the cap from the distal end of the safety shield;

f) inserting an evacuated receptacle, stopper first, into the safety shield until the sharp distal end of the needle cannula pierces the stopper and enters the cavity of the receptacle;

g) allowing blood to flow from the syringe barrel chamber through the needle cannula lumen and into the cavity of the receptacle; and h) removing the receptacle from the safety shield when the desired amount of blood has entered the cavity from the chamber.

An alternative embodiment of the present invention includes a method of delivering a blood sample to an evacuated receptacle having a closed end, an opposed open end, a cylindrical side wall therebetween defining a cavity, and a pierceable stopper occluding the open end, the cavity being at a subatmospheric pressure, comprising the steps of:

a) providing a syringe assembly comprising a syringe barrel having an open proximal end, a distal end and a sidewall therebetween defining a chamber for retaining fluid, a blunt cannula having a blunt distal end and a lumen therethrough connected to the distal end of the syringe barrel so that the lumen is in fluid communication with the chamber, a cylindrical safety shield having an open distal end and an open proximal end, the safety shield is slidably mounted over the syringe barrel for telescoping movement from a proximal position where the blunt cannula projects through the open distal end of the safety shield to a distal position where the safety shield surrounds the blunt cannula, a piston is in fluid-tight slidable engagement inside the barrel and connected to a rigid plunger rod which extends proximally through the open end of the barrel;

b) providing a catheter having a proximal end, a distal end and a passageway therethrough and a housing having a hollow interior in fluid communication with the passageway, the housing having a port extending therefrom the port having a conduit therethrough in fluid communication with the hollow interior, a pre-slit septum sealing the conduit.

c) placing the distal end of the catheter in a mammalian blood vessel;

d) inserting the blunt distal end of the blunt cannula into and through the slit in the septum so that the lumen is in fluid communication with the conduit, and drawing blood from the blood vessel through the catheter, through the hollow interior, the conduit and into the chamber by manipulating the plunger rod;

e) withdrawing the blunt cannula from the slit in the septum;

f) disconnecting the blunt cannula from the barrel;

g) providing a needle cannula having a sharp distal end;

h) connecting the needle cannula to the distal end of the syringe barrel;

i) moving the safety shield to the distal position;

j) inserting the evacuated receptacle, stopper first, into the safety shield until the sharp distal end of the needle cannula pierces the stopper and enters the cavity of the receptacle;

k) allowing blood to flow from the syringe chamber through the lumen into the cavity of the receptacle; and l) removing the receptacle from the safety shield when the desired amount of blood has entered the cavity of the receptacle from the chamber.

BRIEF DESCRIPTION OF THE DRAWINGS

FIG. 3 is a side elevation view of the syringe assembly of FIG. 1 with the needle guard removed;

FIG. 4 is a cross-sectional view of the syringe of FIG. 3 taken along line 4—4;

DETAILED DESCRIPTION

Figure 2:
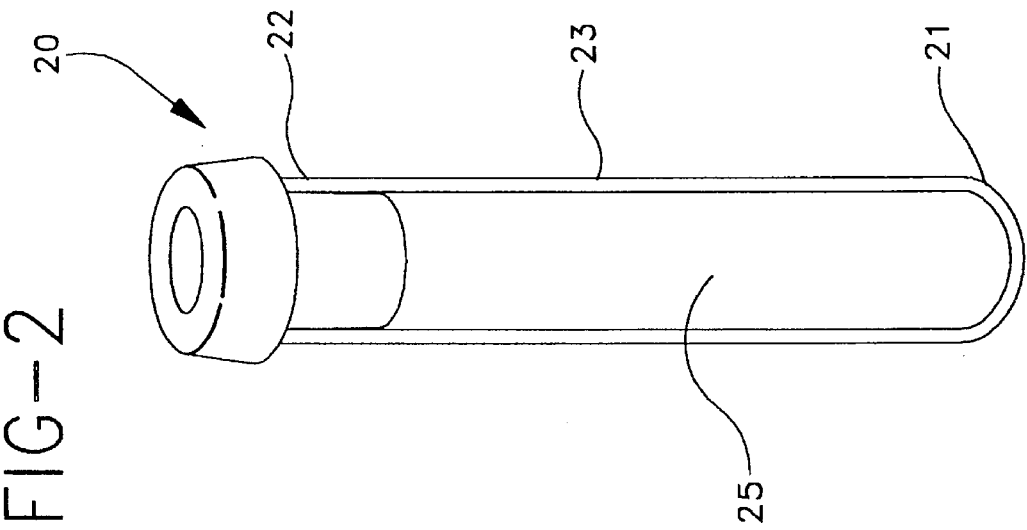
FIG. 2 is a perspective view of an evacuated receptacle having a pierceable stopper.

While this invention is satisfied by embodiments in many different forms, there are shown in the drawings and will herein be described in detail, preferred embodiments of the invention with the understanding that the present disclosure is to be considered exemplary of the principles of the invention and is not intended to limit the invention to the embodiments illustrated. The scope of the invention will be measured by the appended claims and their equivalents.

Adverting to FIGS. 1–10, the present invention relates to a method for delivering a blood sample to an evacuated receptacle. Evacuated blood collection tubes or receptacles are well known in the art and are commercially available. The VACUTAINER Brand Blood Collection Tube manufactured by Becton, Dickinson and Company is the most widely used evacuated blood collection tube. Evacuated receptacles are available with a wide variety of additives such as coagulants, anticoagulants, various compounds to facilitate diagnostic testing, and inert gel materials which provide a barrier to separate the serum after centrifugation of the blood sample. Evacuated receptacles also are available with liquid culture growth medium therein. A typical evacuated receptacle 20 includes a closed end 21 an opposed open end 22, a cylindrical side wall 23 therebetween defining a cavity 25, and a pierceable stopper 26 occluding the open end. Evacuated receptacles may be made with glass or plastic side wall and end portions. The pierceable stopper is made of rubber. Evacuated receptacles are assembled in subatmospheric conditions so that the cavity is evacuated and at a subatmospheric pressure. Receptacles containing culture medium can have a long cylindrical neck portion which holds the stopper and a larger diameter base portion for holding most of the liquid culture medium.

The method of the present invention uses a syringe assembly 28 comprising a syringe barrel 29 having an open proximal end 31 a distal end 32 and a side wall 33 therebetween defining a chamber 34 for retaining fluid. A needle cannula 37 having a sharp distal end 38 and a lumen therethrough is connected to distal end 32 of the syringe barrel so that the lumen is in fluid communication with chamber 34 of the syringe barrel.

It is within the purview of the present invention to include a needle cannula which is permanently attached to the syringe barrel such as through the use of mechanical elements and/or adhesives such as epoxy. In this preferred embodiment the needle cannula is attached to a needle hub 39 having an interior conduit 40. Needle cannula 37 is connected to the needle hub so that the lumen of the needle cannula is in fluid communication with interior conduit 40. Interior conduit 40 is frusto-conically shaped to frictionally engage frusto-conically shaped tip 35 on the distal end of the syringe barrel. The distal end of the syringe barrel also includes locking luer-type collar 36 adjacent to and in spaced concentric relationship around tip 35. Luer collar 36 includes an internal thread 41 to enable threaded mounting of the needle hub between the collar and the syringe tip. Accordingly, the needle assembly which includes needle hub 39 and needle cannula 37 is releasably connected to the syringe barrel. The needle assembly is connected to the syringe barrel by rotating the needle assembly so that projections 43 on the needle hub follow internal thread 41 on the locking luer collar to pull the needle hub axially so that the exterior frusto-conically shaped tip 35 frictionally engages frusto-conically shaped interior conduit 40 of the needle hub. The needle assembly may be disconnected from the hub by rotation of the needle assembly in the direction opposite of that required for installation.

Figure 1:
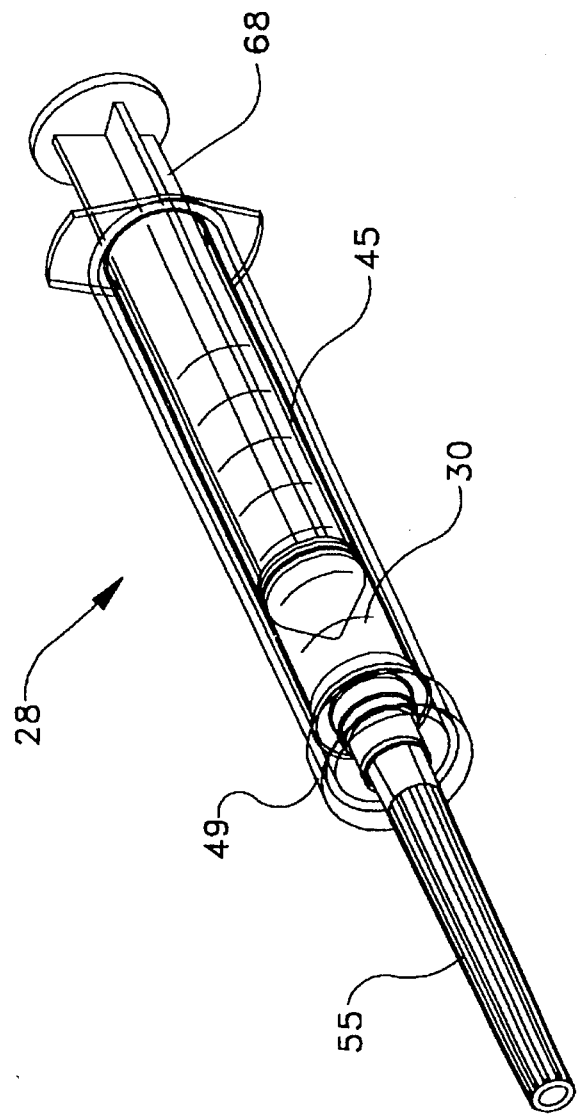
FIG. 1 is a perspective view of a hypodermic syringe having a slidable safety shield.

Syringe assembly 28 includes a cylindrical safety shield 45 having an open distal end 46 and an open proximal end 47. A cap 49 is removably connected to distal end 46 of the safety shield. Cap 49 includes an end wall 50 having aperture 51 therein. The diameter of aperture 51 is less than the inside diameter of safety shield 45 for limiting access to the open distal end of the safety shield to further reduce the probability of accidental needle sticks. The diameter of aperture 51 is also less than the outside diameter of the portion of the evacuated receptacle stopper which is outside of the receptacle. Cap 49 also includes cylindrical side wall 52 preferably having a larger outside diameter than the outside diameter of the safety shield. In the preferred embodiment cylindrical side wall 52 of the cap includes inwardly projecting annular surface 53 which cooperates with outwardly projecting annular surface 48 so that the cap engages the safety shield in a snap-fit type arrangement. Accordingly, the cap can be installed and removed by forces sufficient to overcome the interference between inwardly projecting annular surface 53 on the cap and outwardly projecting annular surface 48 on the safety shield. The syringe as manufactured and delivered preferably contains the cap installed as illustrated in FIGS. 1, 3, 4 and 5. As best illustrated in FIG. 1, a syringe as manufactured preferably contains a rigid removable safety cover 55. This cover frictionally engages the needle hub and is removed and discarded at the time of use either by physically removing the cover from the needle hub or by making the aperture in the cap smaller than the outside diameter of the needle cover so that forward motion of the needle shield dislodges the needle cover from its hub engaging position.

Figure 5:
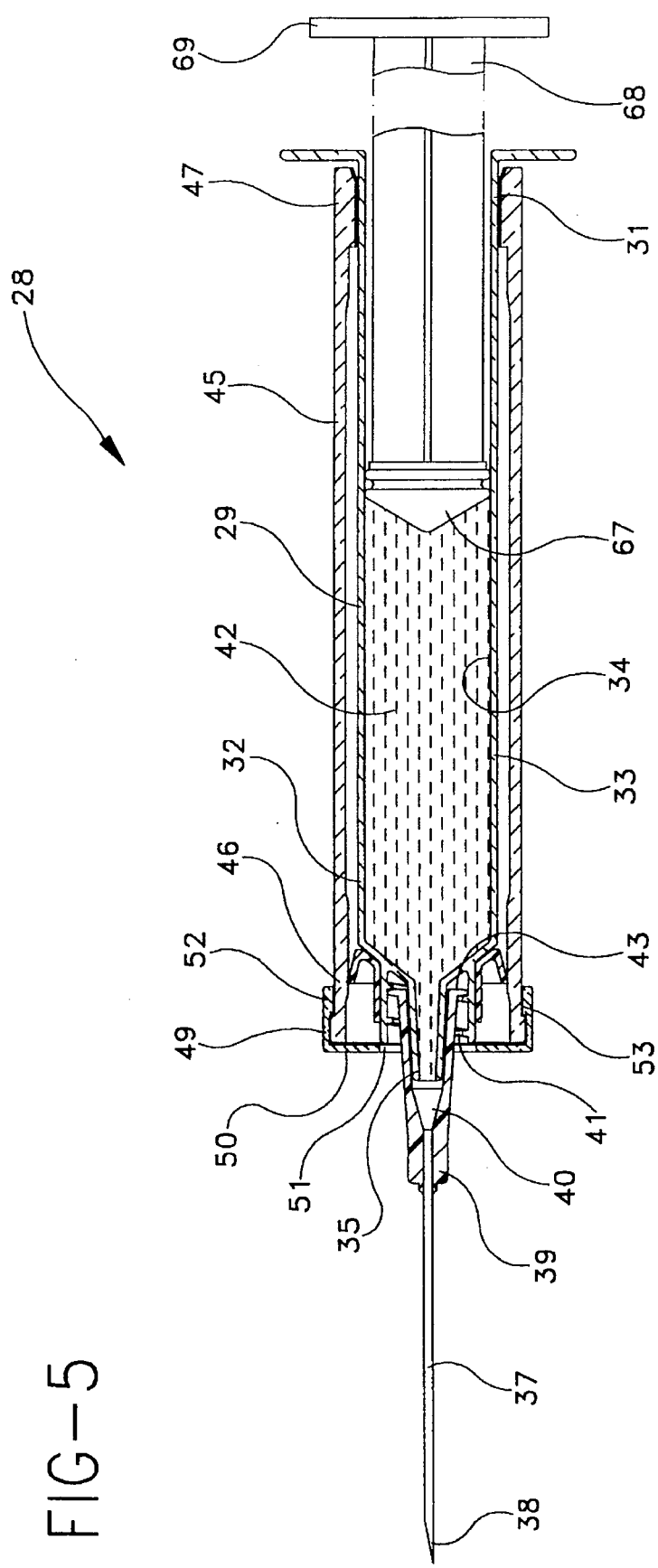
FIG. 5 is a cross-sectional view, similar to FIG. 4, illustrating the syringe assembly containing blood drawn from a patient.
Figure 6:
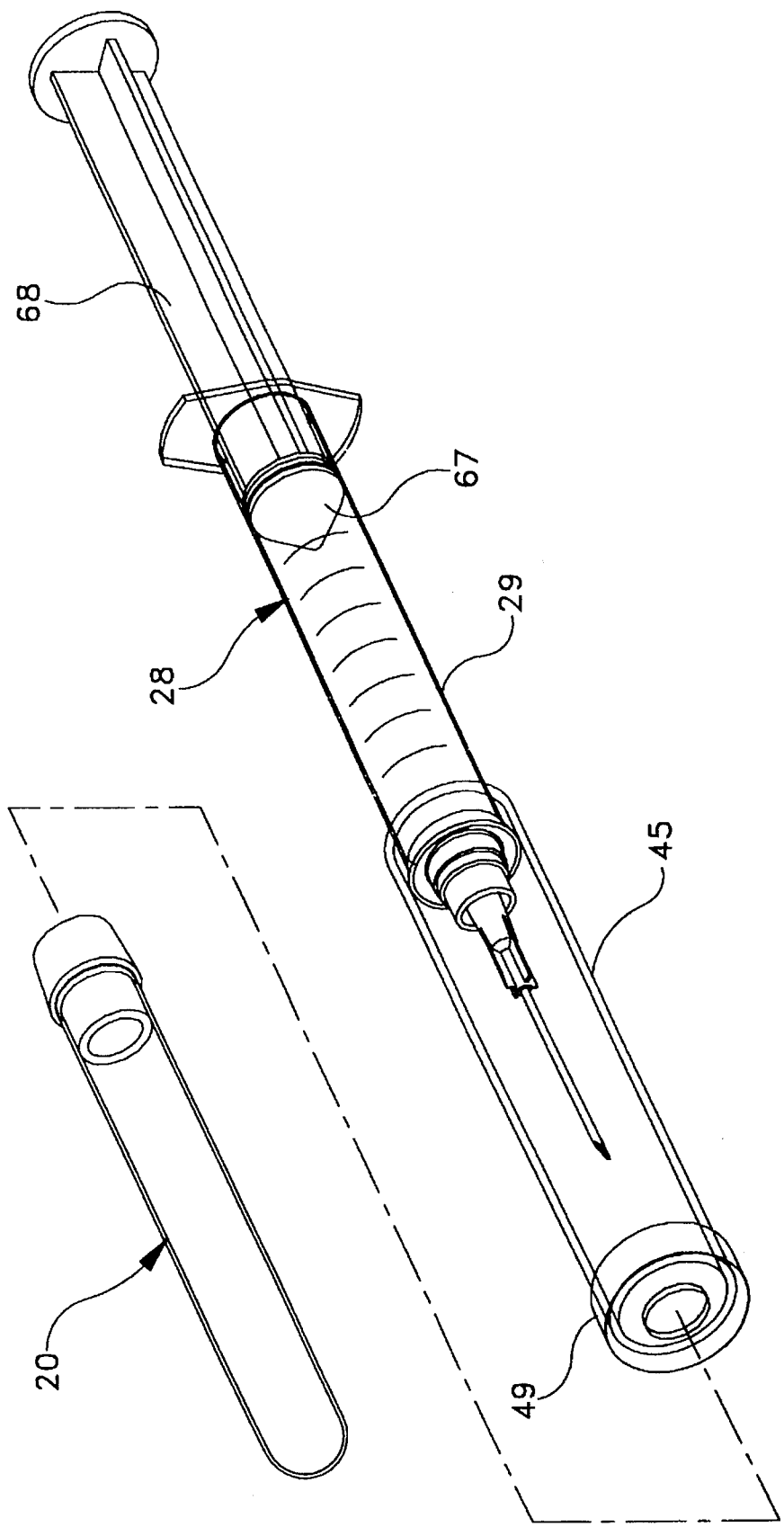
FIG. 6 is an exploded view showing an evacuated receptacle and the syringe of FIG. 5 with its safety shield in a distal needle protecting position.
Figure 8:
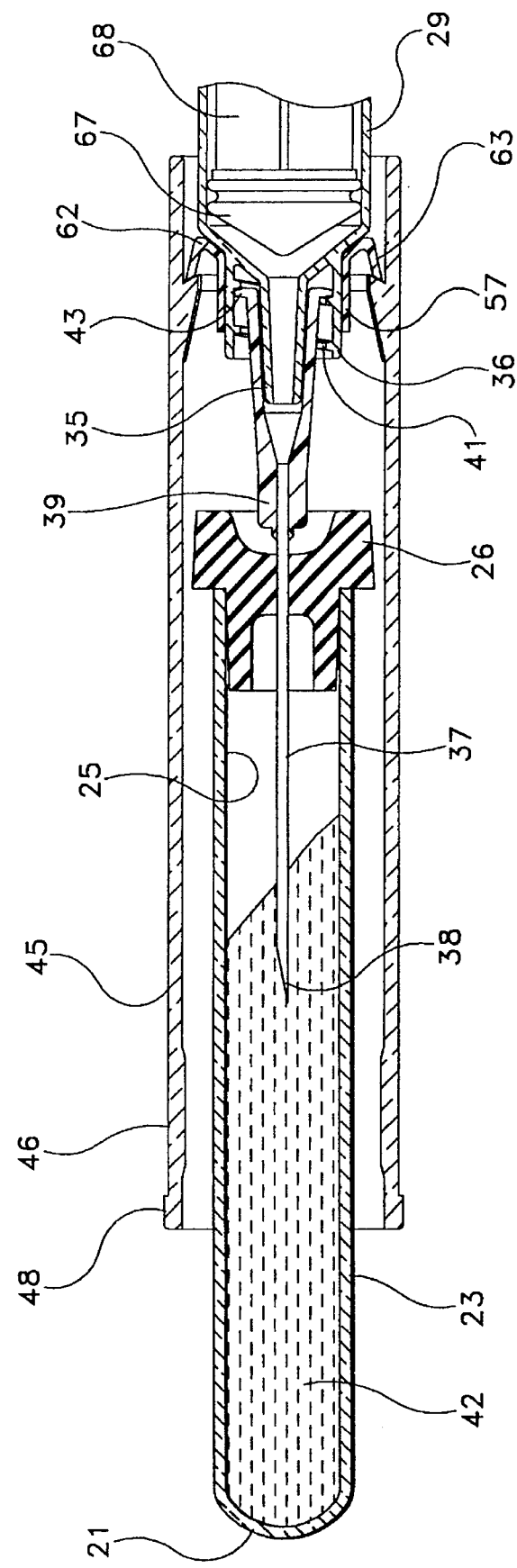
FIG. 8 is a partial cross-sectional view of the syringe assembly and evacuated receptacle of FIG. 7 taken along line 8—8.
Figure 10:
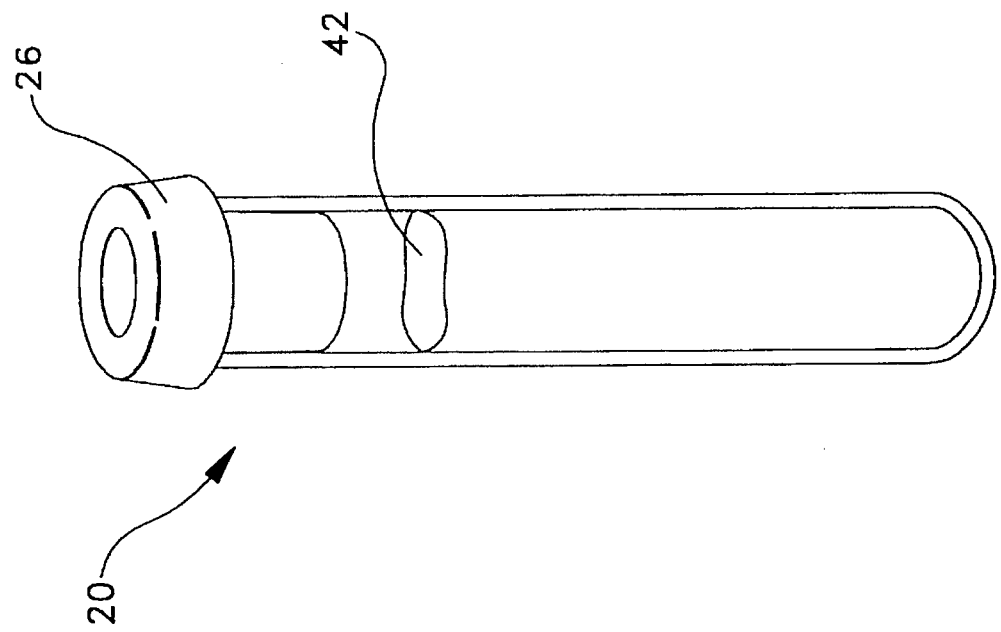
FIG. 10 is an evacuated receptacle containing a blood sample.
Figure 9:
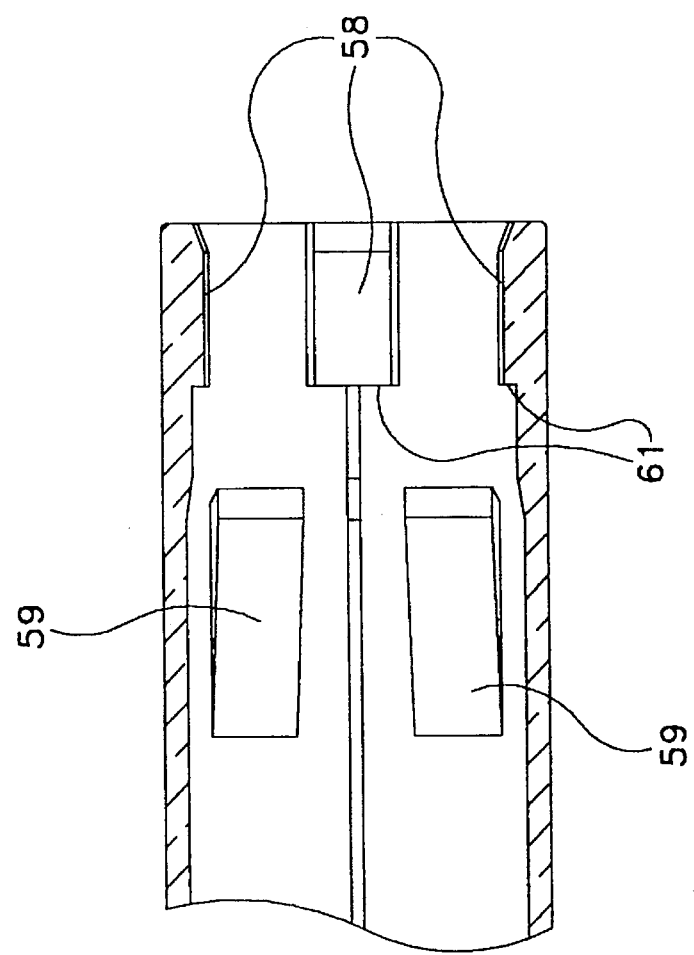
FIG. 9 is a partial cross-sectional view of the safety shield illustrating locking projections for preventing movement of the safety shield after it is in the distal needle protecting position.

Safety shield 45 is slidably mounted over syringe barrel 29 for telescoping movement from a proximal position as best illustrated in FIGS. 3–5, where the needle cannula projects through aperture 51 of cap 49, to a distal position, as best illustrated in FIGS. 6 and 8, where the safety shield protectively surrounds the needle cannula.

In the preferred embodiment, safety shield 45 can be locked in the distal needle protecting position. Locking is achieved through cooperation between collar 57 on the distal end of the syringe barrel and inwardly projecting stop locks 58 and ramped locking teeth 59 at the proximal end of the safety shield. In particular, collar 57 includes solid annular stop wall 62 which includes distally extending frusto-conically shaped projection 63. Collar 57 is fixedly attached to the distal end of the syringe barrel through the use of adhesives or mechanical means. The collar can also be attached to or be an integral part of the needle hub. As the safety shield is telescoped from the proximal position to the distal position, distally extending frusto-conically shaped projection 63 deflects as it passes over the ramped locking teeth and becomes trapped between ramped locking teeth 59 and stop surfaces 61 on stop locks 58. At this position the safety shield cannot be returned to the proximal position.

U.S. Pat. No. 5,169,392 also teaches a syringe assembly having a safety shield, a collar mounted on the distal end of the syringe barrel and inwardly directed projections on the proximal end of the safety shield positioned to cooperate with the collar for releasably holding the safety shield when the shield is in the distal needle protecting position. Specifically, U.S. Pat. No. 5,169,392 teaches a syringe and needle assembly wherein the shield can move back and forth over the barrel of the syringe to alternately expose or shield the needle tip from user contact. The collar and shield structure allows the needle shield to be in the fully extended position and not locked. In order to lock the safety shield in the fully extended position the shield must be rotated with respect to the barrel so that inwardly directed projections or keys on the inside surface of the shield will snap over angled surfaces on the collar and be locked in blind slots so that proximal motion of the sleeve with respect to the barrel will be resisted by surfaces on the keys which abut against squared-off surfaces of the blind slots. Syringes like the syringe taught in U.S. Pat. 5,169,392 are suitable for use in and are within the purview of the method of the present invention.

A piston 67 is in fluid-tight slidable engagement inside the syringe barrel. An elongate rigid plunger rod 68 is connected to the piston and extends proximally through open proximal end 31 of the barrel.

The method of the present invention includes providing a syringe assembly of the type having a safety shield and a removable cap such as described or as referred to hereinabove. With the safety shield in the proximal needle exposing position, the sharp distal end of the needle cannula is urged into a mammalian blood vessel such as the vein of a patient until fluid communication is established o between the lumen of the needle and the interior of the blood vessel. The user then applies a gentle, proximally directed force on plunger rod 68, through plunger rod flange 69 to draw blood from the blood vessel into chamber 34 of the syringe barrel so that the chamber contains the desired quantity of blood, indicated by numeral 42. To determine the volume of blood in the syringe barrel, volume measuring indicia printed on the outside diameter of the cylindrical side wall, as best illustrated in FIG. 1, are provided. When the desired amount of blood is obtained the needle cannula is withdrawn from the blood vessel.

The user then telescopes safety shield 45 to the distal needle protecting position. It is preferred that when the safety shield is in the distal needle protecting position it is locked in the distal position and incapable of returning to a needle exposing position through structure involving cooperating structure on the barrel and the inside of the safety shield. The preferred embodiment includes a collar and inwardly directed projections in the proximal end of the safety shield. The projections in the safety shield cooperate with the collar when the safety shield is in the distal needle protecting position to lock the shield in the distal needle protecting position for preventing exposure of the sharpened distal tip of the needle cannula. Other cooperating structure between a collar on the syringe barrel and projections on the inside of a safety shield, such as that taught in U.S. Pat. No. 5,169,392, allows the safety shield to be releasably held in the distal needle protecting position. Both structures are within the purview of the present invention.

Figure 7:
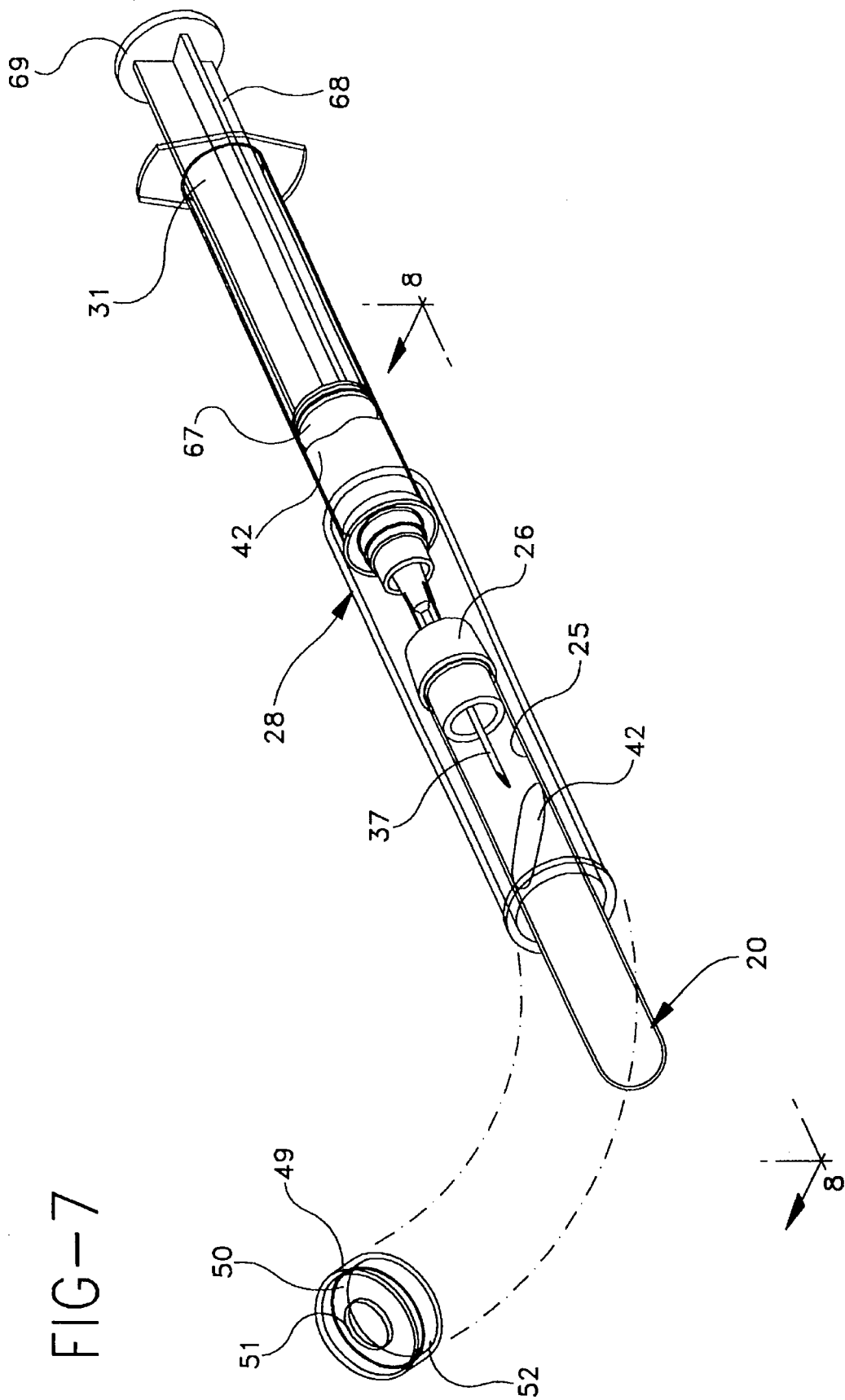
FIG. 7 is an exploded view illustrating the cap removed from the safety shield and the evacuated receptacle inserted in the safety shield with the needle cannula piercing the pierceable stopper and blood entering the evacuated receptacle.

With the safety shield in the distal position, the user then removes cap 49, as illustrated in FIG. 7 so that the opening in the distal end of the safety shield is now large enough to accept an evacuated receptacle. The user then inserts evacuated receptacle 20, with stopper 26 first, into the safety shield until sharp distal end 38 of the needle cannula pierces pierceable stopper 26 of the evacuated receptacle and enters cavity 25 of the tube. The subatmospheric pressure in the tube should be sufficient to allow the atmospheric pressure to move the plunger rod distally and allow blood to enter the evacuated receptacle. Accordingly, in most situations, the user will observe the movement of the plunger rod and will allow blood to flow from the syringe chamber through the lumen of the needle cannula into the cavity of the tube until the desired amount of blood has entered the cavity from the chamber in the barrel. Although not preferred, the plunger rod 69 may be manipulated to urge blood from the syringe barrel into the receptacle. When the desired amount of blood has entered the receptacle, the user removes the receptacle from the safety shield.

It is within the purview of the present invention to include a method of delivering a blood sample to an evacuated receptacle wherein the syringe assembly does not have a removable cap, such as removable cap 49. All of the steps in this method will be identical to the steps using the syringe assembly with the removable cap except that the step of removing the cap is eliminated because the cap is not part of the syringe assembly.

The syringe assembly containing blood, may then be used to provide blood to one or more additional evacuated receptacles by following the same steps as described hereinabove. Specifically, the user provides a second evacuated receptacle and inserts this receptacle, stopper first, into the safety shield until the sharp distal end of the needle cannula pierces the stopper and enters the cavity. The user then allows blood to flow from the syringe chamber through the lumen of the needle cannula into the cavity of the second evacuated receptacle. When the desired amount of blood has entered the second receptacle it is removed from the safety shield of the syringe assembly.

In some instances it is desired to culture the patient's blood to determine the existence of bacteria using culture medium containing receptacles described above. When testing for bacteria it is often desirable to disconnect the needle cannula from the syringe barrel after the needle cannula is withdrawn from the patient's blood vessel. This needle cannula is discarded because it may contain bacteria which came from the surface of the patient's skin and not from the patient's blood. At this point, the user provides a second needle cannula and connects the second needle cannula to the distal end of the syringe barrel. The safety shield may now be telescoped to the distal needle protecting position and the additional steps, described hereinabove, may be practiced. It is preferred that the syringe barrel have a chamber volume of at least 10 cc.

Although most blood samples are taken from the patient's blood vessel, it is not necessary for the blood sample to be taken directly from the blood vessel and it is within the purview of the present invention to include methods wherein the blood sample is taken from a device, such as a catheter assembly, which is in fluid communication with a mammalian blood vessel. Many hospital patients have, in accordance with their therapy, an I.V. catheter connected to a vein ready for use in various procedures or in fluid communication with an I.V. system for infusing liquids and medication into the patient. Many I.V. sets have side ports which allow access for the purpose of injecting medication into the patient, providing anticoagulants and the like. Taking a blood sample from a remote in-dwelling site has the advantage of not having to pierce the patient's vein each time a blood sample is taken. This is particularly helpful in patients having veins which are difficult to access and patients who have been under long term care in order to avoid scarring of the vessels through repeated venipuncture.

Figure 11:
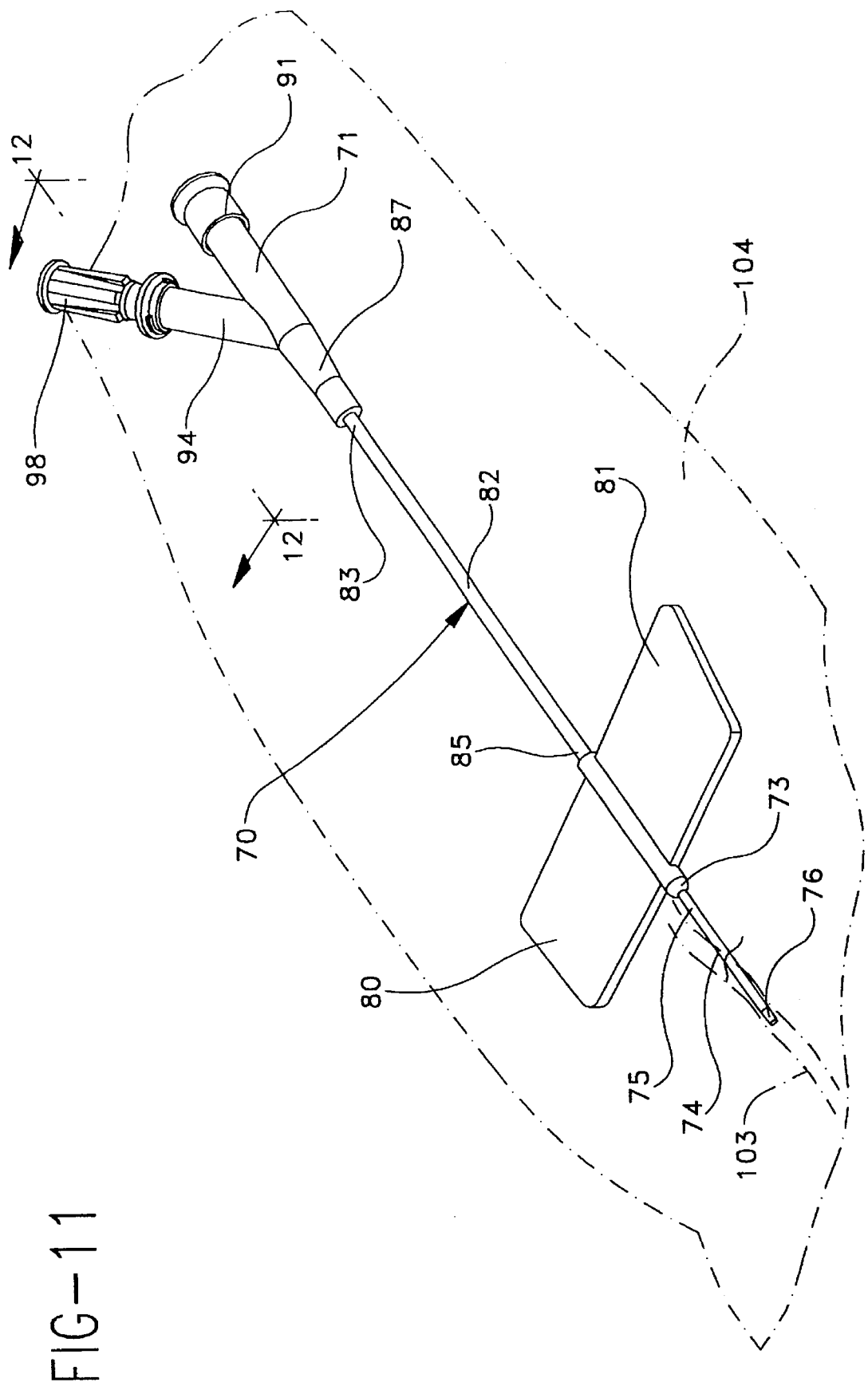
FIG. 11 is a perspective view of a catheter assembly with the catheter inserted in a patient's blood vessel.
Figure 12:
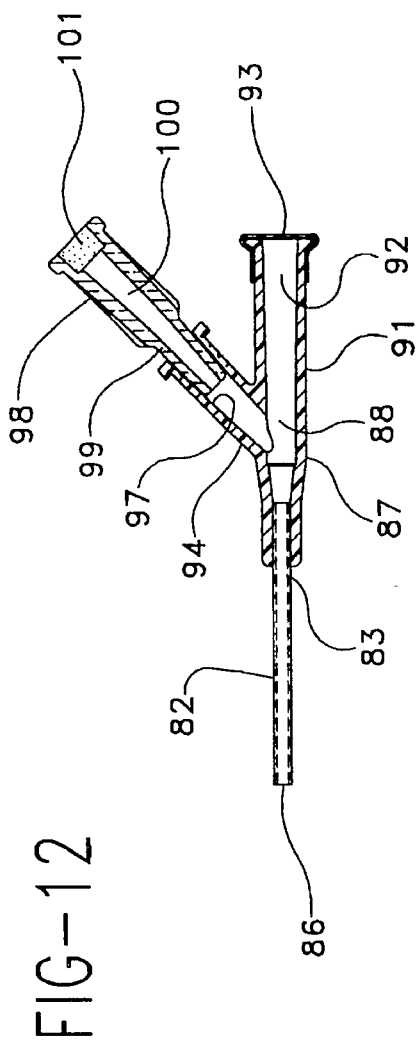
FIG. 12 is a cross-sectional view of the housing of the catheter assembly of FIG. 11 taken along line 12—12.
Figure 13:
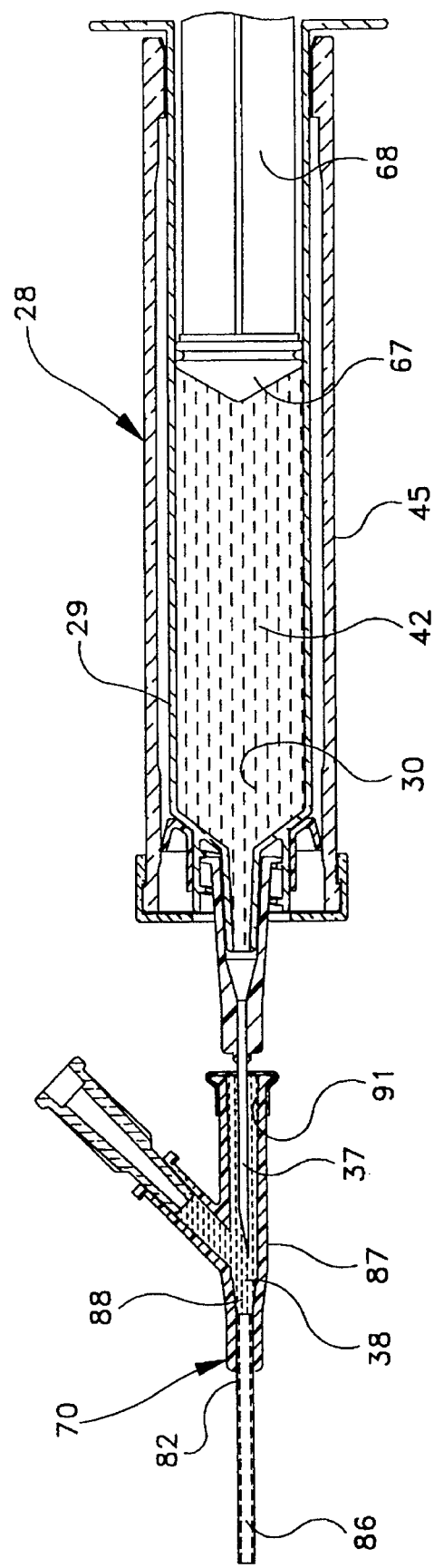
FIG. 13 is a cross-sectional view illustrating the syringe of FIG. 1 with its needle cannula piercing the pierceable septum of the housing of FIG. 12 and blood being drawn from a patient.

Referring to FIGS. 11–13, a catheter assembly 70 is representative of many commercially available catheter assemblies which can be used to achieve remote access to a patient's vascular system. Catheter assembly 70 includes proximal end 71 and distal end 73. The distal end of the catheter assembly includes catheter 74 having a proximal end 75 and a distal end 76 and a passageway therethrough. Proximal end 75 of the catheter is connected to intermediate member 79 containing wings 80 and 81. Wings 80 and 81 are flexible and can be used to guide the insertion of the catheter into the blood vessel and also used as a structure to hold the catheter assembly in place using tape. Catheter assemblies without wings are also known in the art. A flexible tube 82 includes proximal end 83 and distal end 85 and a fluid conduit 86 therethrough. Flexible tube 82 is connected to the catheter via intermediate member 79 so that fluid conduit 86 of the flexible tube is in fluid communication with the passageway of the catheter. Proximal end 83 of flexible tube 82 is connected to a housing 87 having a hollow interior 88, in fluid communication with fluid conduit 86 of the flexible tube. Housing 87 includes port 91 having a conduit 92 therethrough in communication with the hollow interior and a pierceable septum 93 sealing the conduit. The septum can cover the end of the conduit or be positioned within the conduit. Ports covered by pierceable septums are known in the art and sometimes referred to as "PRN" from the Latin "pro re nata" meaning "as the need arises." Septum 93 is preferably made of rubber or other elastomeric material which permits the insertion of a sharp needle cannula in order to infuse or withdraw fluids through the catheter. On withdrawal of the needle cannula the septum reseals itself. Also, as will be discussed in more detail hereinafter, septums may be pre-slit to facilitate the insertion of a blunt cannula rather than a sharp needle.

In the embodiment illustrated, housing 87 includes a second port 94 having a conduit 95 therethrough in fluid communication with hollow interior 88. Second port 94 also includes a frusto-conically shaped recess 97 in fluid communication with conduit 95. While not in use, second port 94 is sealed by vent plug 98 which includes a frusto-conically shaped tip 99 which frictionally engages the frusto-conically shaped recess of the second port to seal conduit 95. Vent plug 98 also includes a hollow interior 100 covered by an air permeable, liquid impermeable element 101 which allows air to escape from the housing interior when liquid enters the interior. However, liquid such as blood or I.V. fluid cannot pass through the element.

Methods and apparatus for placing the catheter in fluid communication with a mammalian vessel, such as a patient's vein, are well known in the art. Usually the catheter is inserted with the help of a needle which pierces the wall of the vein. In a catheter over needle design, the needle is placed inside the catheter and projects beyond the distal end of the catheter. Usually the catheter is tapered to provide a smooth transition between the outside of the diameter of the needle and the outside diameter of the catheter. The sharpened needle, with catheter attached, is advanced to pierce the patient's vein. When the distal end of the catheter is within the vein, the needle is withdrawn through the catheter leaving only the soft catheter in the vein. The catheter with a needle contained therein is described in U.S. Pat. No. 5,409,461. There are also catheter assemblies and procedures wherein the catheter is placed within the needle and the catheter is advanced through the needle after fluid communication with the vessel is established.

An alternative method of the present invention involves the steps of taking the blood sample from a remote site in fluid communication with the patient's vascular system using a hypodermic syringe having a safety shield and transferring the blood sample to an evacuated receptacle. This alternate method of the present invention uses syringe assembly 28 described hereinabove and illustrated in FIGS. 1, and 3–9. The alternative method is similar to the method described hereinabove and illustrated in FIGS. 1–10 except for the steps involving providing a catheter, such as catheter 74 in catheter assembly 70. The catheter assembly includes a housing, such as housing 87, having a hollow interior in fluid communication with the passageway of the catheter. It is within the purview of the present invention to include housing structures connected directly to the catheter and housing structures connected to the catheter through intermediate fluid conduits such as intermediate member 79 and flexible tube 82 of catheter assembly 70. This alternate method involves placing the distal end of the catheter into a mammalian blood vessel such as the patient's vein. Placing the catheter in the patient's vein is well known in the art, described hereinabove and illustrated in FIG. 11 wherein catheter 74 is illustrated in the patient's vein 103 of the patient's arm 104, both illustrated in phantom. When the catheter is in fluid communication with the patient's vein blood will flow from the vein through the catheter into the housing with air escaping through vent plug 98. The blood sample is taken from the patient by piercing pierceable septum 93 with sharp distal end 38 of needle cannula 37 so that the lumen of the needle cannula is in fluid communication with conduit 91 of housing 87. Blood is then drawn from the blood vessel through the catheter, through fluid conduit 86 of flexible tube 82, into hollow interior 88 of housing 87, through conduit 91, through the lumen of the cannula and into chamber 30 of syringe barrel 29. The remainder of this alternative method of the present invention, after blood is drawn into the syringe barrel chamber, is described hereinabove and illustrated in FIGS. 1–10.

It should be noted that this alternative method using a catheter assembly can also be practiced with the syringe assembly which does not have a cap removably connected to the distal end of the safety shield. This further alternative method is substantially identical except that the step of removing the cap will not be required since the cap is not present.

Figure 14:
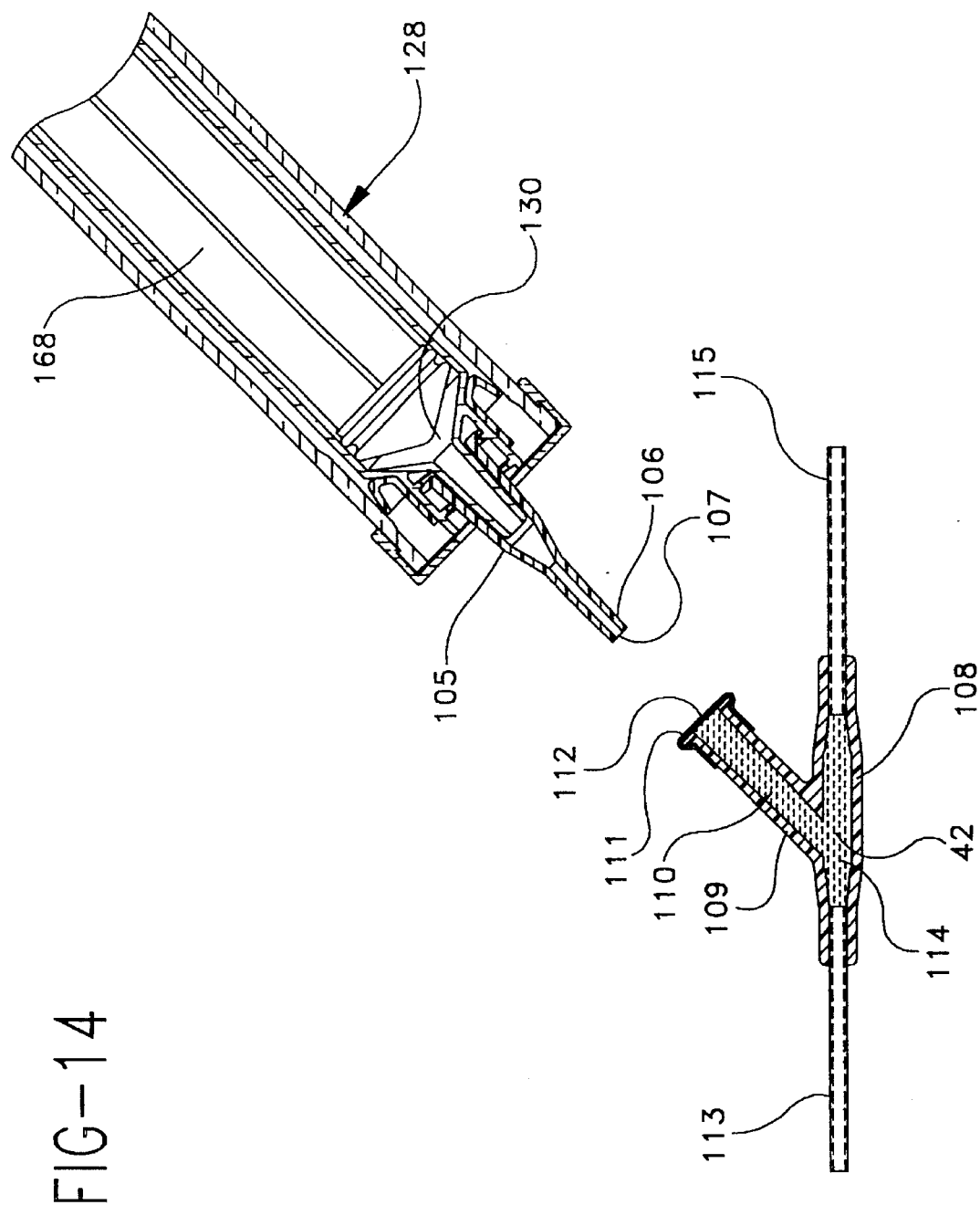
FIG. 14 is a cross-sectional view of an alternative embodiment, similar to FIG. 13, having a pre-slit septum and a blunt cannula.

Referring to FIGS. 1–14, with particular emphasis to FIG. 14, another alternative embodiment of the method of the present invention involves taking a blood sample to a remote site for subsequent placement into an evacuated receptacle. In this alternative embodiment, syringe assembly 128 is substantially identical to syringe assembly 28 except that a sharpened needle cannula is replaced by blunt cannula 105 having a blunt distal end 106 and a lumen 107 therethrough. The housing used to practice this alternative method is a housing 108 having a hollow interior 114 and a port 109 in fluid communication with the hollow interior of the housing. Port 109 includes conduit 110 covered by septum 111 having a slit therein. Septum 111 effectively seals conduit 110 from the exterior of the housing. However, access to the conduit can be achieved by pressing the blunt distal end 106 of blunt cannula 105 against the area of the septum containing slit 112. Gentle force applied to the syringe assembly in an axial direction will cause the blunt distal end of the blunt cannula to enter the conduit through the slit which is forced open by the blunt cannula. Upon removing the blunt cannula from the conduit the slit portion of the septum will automatically seal itself. Housing 108 is connected to catheter 113 which is in fluid communication with the patient's vein (not shown). Flexible tube 115 is also connected to the housing and contains apparatus (not shown) which allows it to be connected to and in fluid communication with other fluid delivery apparatus such as a bag or a bottle containing intravenous solution. In this alternative method the steps are substantially identical to the method described hereinabove and illustrated in FIGS. 11–13 except for the blunt cannula and pre-slit septum. This alternative method involves inserting blunt distal end 106 of blunt cannula 105 into and through the slit 112 of the septum 113 so that the lumen 107 is in fluid communication with conduit 110, and drawing blood 42 from the blood vessel through catheter 113 and hollow interior 114, through conduit 110, lumen 107 and into chamber 130 of syringe barrel 128 by manipulating the plunger rod 168.

It should be noted that this alternative method can also be practiced with a syringe assembly not having a removable cap. The steps of practicing the alternative method will remain the same except that it will not be necessary to remove the cap since it had been removed or was not present at the start of the procedure.

Figure 15:
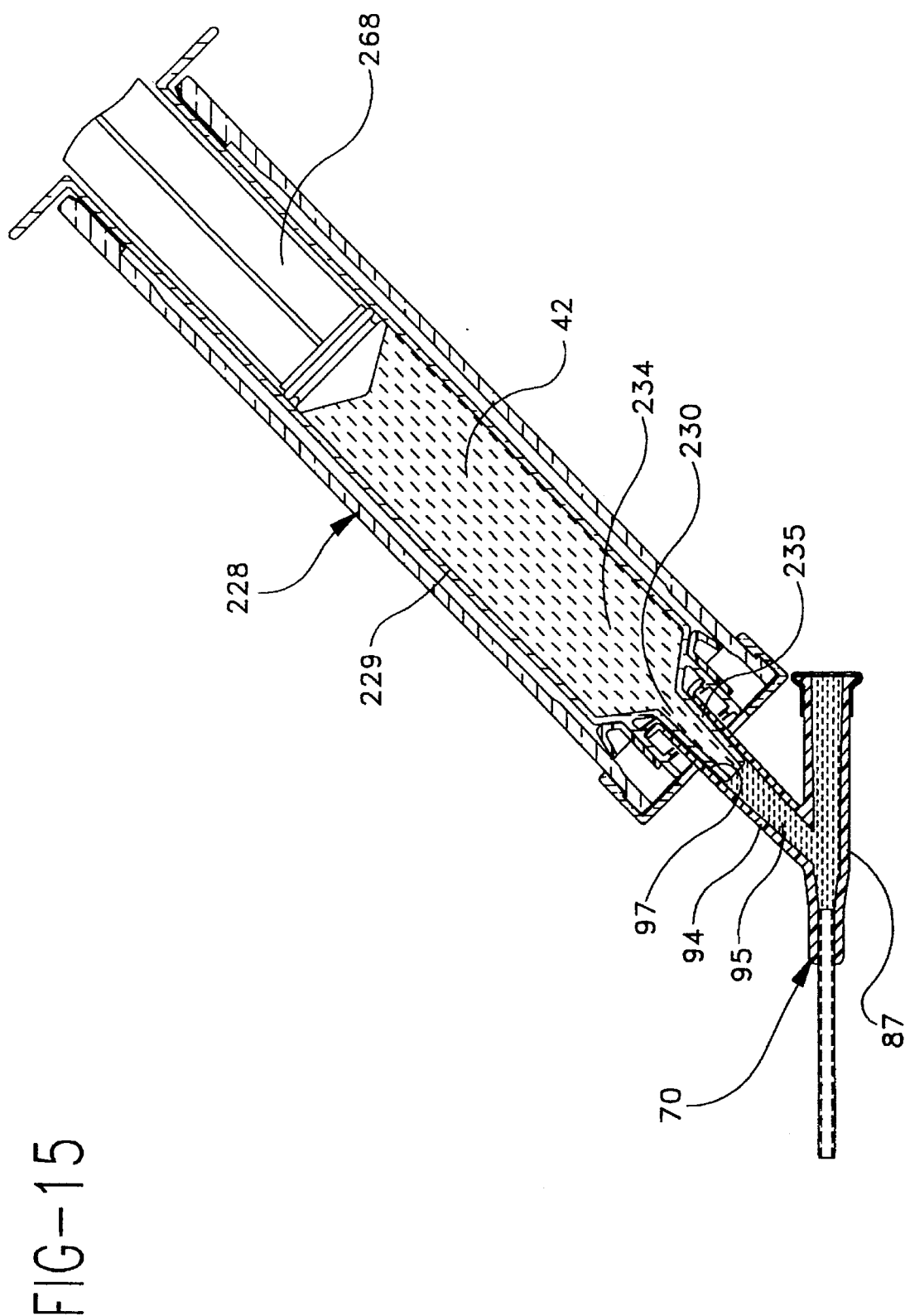
FIG. 15 is an alternative embodiment of the present invention similar to FIG. 13, wherein the blood sample is taken without the use of the needle cannula.

Another alternative method of the present invention is best illustrated in FIGS. 1–13 and 15 with particular emphasis on FIG. 15. In this alternative method the transfer of the blood 42 from the patient's vein to chamber 230 of syringe assembly 228 is accomplished without the use of the needle cannula having a sharp distal end in conjunction with the pierceable septum or without a blunt cannula in conjunction with a pre-slit septum. This alternative method can be carried out using catheter assemblies such as catheter assembly 70 and syringe assembly 28 with needle cannula 37 removed. As recited hereinabove, housing 87 includes port 94 having conduit 95. Conduit 95 includes a frusto-conically shaped recess 97 which is shaped to engage the frusto-conically shaped outer surface of tip 235 of syringe barrel 229. This alternative method is substantially similar to the methods described hereinabove, however, blood 42 is delivered to cavity 230 of syringe barrel 229 by inserting the frusto-conically shaped tip of syringe barrel 229 into frusto-conically shaped recess 97 of port 94 so that fluid path 230 of tip 235 is in fluid communication with conduit 95. Blood is then drawn from the blood vessel through the catheter, through the hollow interior of the housing and the conduit and into chamber 34 by manipulating plunger rod 68.

It should also be noted that this alternative method can be practiced using a syringe assembly which does not have a removable cap. In this alternative method the step of removing the cap will not be necessary since the cap is not included with the syringe assembly.

The present invention provides a method for withdrawing blood from a patient using a hypodermic syringe and delivering the blood to one or more evacuated receptacles or other test devices using a hypodermic syringe having a telescoping safety shield with or without a removable cap which will reduce the possibility of accidental needle sticks during this procedure.

What is claimed is:

1. A method of delivering a blood sample to an evacuated receptacle having a closed end, an opposed open end, a cylindrical side wall therebetween defining a cavity, and a pierceable stopper occluding the open end, the cavity being at a subatmospheric pressure, comprising the steps of:

(a) providing a syringe assembly comprising a syringe barrel having an open proximal end, a distal end and a side wall therebetween defining a chamber for retaining fluid, a needle cannula having a sharp distal end and a lumen therethrough connected to said distal end so that said lumen is in fluid communication with said chamber, a cylindrical safety shield having an open distal end and a open proximal end, a cap removably connected to said distal end of said safety shield, said cap having an aperture smaller than the inside diameter of said open distal end of said shield for limiting access to said open distal end of said shield, said safety shield slidably mounted over said syringe barrel for telescoping movement from a proximal position where said needle cannula projects through said aperture to a distal position where said safety shield protectively surrounds said needle cannula, a piston in fluid-tight slidable engagement inside said barrel, a rigid elongate plunger rod connected to said piston and extending proximally through said open proximal end of said barrel;

(b) providing a catheter having a proximal end, a distal end and a passageway therethrough and a housing having a hollow interior in fluid communication with said passageway, said housing having a port extending therefrom, said port having a conduit therethrough in fluid communication with said hollow interior, a pierceable septum sealing said conduit;

(c) placing said distal end of said catheter in a mammalian blood vessel;

(d) piercing said pierceable septum with said sharp distal end of said needle so that said lumen is in fluid communication with said conduit and drawing blood from said blood vessel through said catheter, said hollow interior, said conduit and into said chamber by manipulating said plunger rod;

(e) withdrawing said needle from said pierceable septum;

(f) moving said safety shield to said distal needle protecting position;

(g) removing said cap from said distal end of said safety shield;

(h) inserting said evacuated receptacle, stopper first, into said safety shield until said sharp distal end of said needle cannula pierces said stopper and enters said cavity of said receptacle;

(i) allowing blood to flow from said syringe chamber through said lumen into said cavity of said receptacle; and (j) removing said receptacle from said safety shield when the desired amount of blood has entered said cavity of said receptacle from said chamber.

2. The method of claim 1 further comprising the additional steps of:

(k) providing a second evacuated receptacle having a closed end, an opposed open end, a cylindrical side wall therebetween defining a cavity, and a pierceable stopper occluding the open end, the cavity being at subatmospheric pressure;

(l) inserting said second evacuated receptacle, stopper first, into said safety shield until said sharp distal end of said needle cannula pierces said stopper and enters said cavity;

(m) allowing blood to flow from said syringe chamber through said lumen into said cavity of said second evacuated receptacle; and (n) removing said second receptacle from said safety shield when the desired amount of blood has entered said cavity from said chamber.

3. The method of claim 1 wherein said needle cannula is removably connected to said distal end of said syringe barrel.

4. The method of claim 3 including the additional steps immediately after withdrawing said needle from said pierceable septum, said steps comprising:

(e1) disconnecting said needle cannula from said barrel;

(e2) providing a second needle cannula; and (e3) connecting said second needle cannula to said distal end of said syringe barrel.

5. The method of claim 1 wherein the step of providing a syringe assembly includes a syringe without a cap removably connected to the distal end of the safety shield and the step of removing the cap from the distal end of the safety shield is eliminated.

6. The method of claim 1 wherein said syringe barrel includes a collar connected to said distal end of said syringe barrel and inwardly directed projections in said proximal end of said safety shield positioned to cooperate with said collar when said safety shield is in said distal needle protecting position to lock said shield in said distal needle protecting position for preventing re-exposure of said sharpened distal end of said needle cannula.

7. The method of claim 1 wherein said syringe barrel includes a collar connected to said distal end of said syringe barrel and inwardly directed projections in said proximal end of said safety shield positioned to cooperate with said collar for releasably holding said shield when said safety shield is in said distal needle protecting position.

8. A method of delivering a blood sample to an evacuated receptacle having a closed end, an opposed open end, a cylindrical side wall therebetween defining a cavity, and a pierceable stopper occluding the open end, the cavity being at a subatmospheric pressure, comprising the steps of:

(a) providing a syringe assembly comprising a syringe barrel having an open proximal end, a distal end and a side wall therebetween defining a chamber for retaining fluid, a blunt cannula having a blunt distal end and a lumen therethrough removably connected to said distal end so that said lumen is in fluid communication with said chamber, a cylindrical safety shield having an open distal end and an open proximal end, a cap removably connected to said distal end of said safety shield, said cap having a aperture smaller than the inside diameter of said open distal end of said shield for limiting access to said open distal end of said shield, said safety shield slidably mounted over said syringe barrel for telescoping movement from a proximal position where said blunt cannula projects through said aperture to a distal position where said safety shield protectively surrounds said blunt cannula, a piston in fluid-tight slidable engagement inside said barrel, a rigid elongate plunger rod connected to said piston and extending proximally through said open proximal end of said barrel;

(b) providing a catheter having a proximal end, a distal end and a passageway therethrough and a housing having a hollow interior in fluid communication with said passageway, said housing having a port extending therefrom, said port having a conduit therethrough in fluid communication with said hollow interior, a pre-slit septum sealing said conduit;

(c) placing said distal end of said catheter in a mammalian blood vessel;

(d) inserting the blunt distal end of said blunt cannula into and through the slit in said septum so that said lumen is in fluid communication with said conduit, and drawing blood from said blood vessel through said catheter, said hollow interior, said conduit and into said chamber by manipulating said plunger rod;

(e) withdrawing said blunt cannula from said slit in said septum;

(f) disconnecting said blunt cannula from said barrel;

(g) providing a needle cannula having a sharp distal end;

(h) connecting said needle cannula to said distal end of said syringe barrel;

(i) moving said safety shield to said distal position;

(j) removing said cap from said distal end of said safety shield;

(k) inserting said evacuated receptacle, stopper first, into said safety shield until said sharp distal end of said needle cannula pierces said stopper and enters said cavity of said receptacle;

(l) allowing blood to flow from said syringe chamber through said lumen into said cavity of said receptacle; and (m) removing said receptacle from said safety shield when the desired amount of blood has entered said cavity of said receptacle from said chamber.

9. The method of claim 8 further comprising the additional steps of:

(n) providing a second evacuated receptacle having a closed end, an opposed open end, a cylindrical side wall therebetween defining a cavity, and a pierceable stopper occluding the open end, the cavity being at subatmospheric pressure;

(o) inserting said second evacuated receptacle, stopper first, into said safety shield until said sharp distal end of said needle cannula pierces said stopper and enters said cavity;

(p) allowing blood to flow from said syringe chamber through said lumen into said cavity of said second evacuated receptacle; and (q) removing said second receptacle from said safety shield when the desired amount of blood has entered said cavity from said chamber.

10. The method of claim 8 wherein the step of providing a syringe assembly includes a syringe without a cap removably connected to the distal end of the safety shield and the step of removing the cap from the distal end of the safety shield is eliminated.

11. The method of claim 8 wherein said syringe barrel includes a collar connected to said distal end of said syringe barrel and inwardly directed projections in said proximal end of said safety shield positioned to cooperate with said collar when said safety shield is in said distal position to lock said shield in said distal position for preventing re-exposure of said sharp distal end of said needle cannula.

12. The method of claim 8 wherein the step of providing a syringe assembly includes a syringe without a cap removably connected to the distal end of the safety shield and the step of removing the cap from the distal end of the safety shield is eliminated.

13. A method of delivering a blood sample to an evacuated receptacle having a closed end, an opposed open end, a cylindrical side wall therebetween defining a cavity, and a pierceable stopper occluding the open end, the cavity being at a subatmospheric pressure, comprising the steps of:

(a) providing a syringe assembly comprising a syringe barrel having an open proximal end, a distal end and a side wall therebetween defining a chamber for retaining fluid, a frusto-conically shaped tip at said distal end having a fluid path therethrough in fluid communication with said chamber, a cylindrical safety shield having an open distal end and an open proximal end, a cap removably connected to said distal end of said safety shield, said cap having an aperture smaller than the inside diameter of said open distal end of said shield for limiting access to said open distal end of said shield, said safety shield slidably mounted over said syringe barrel for telescoping movement from a proximal position where said needle cannula projects through said aperture to a distal position where said safety shield protectively surrounds said needle cannula, a piston in fluid tight slidable engagement inside said barrel, a rigid elongate plunger rod connected to said piston and extending proximally through said open proximal end of said barrel;

(b) providing a catheter having a proximal end, a distal end and a passageway therethrough and a housing having a hollow interior in fluid communication with said passageway, said housing having a port extending therefrom said port having a conduit therethrough in fluid communication with said hollow interior, said port including a frusto conically shaped recess in fluid communication with said conduit;

(c) placing said distal end of said catheter in a mammalian blood vessel;

(d) inserting said frusto-conically shaped tip of said syringe barrel into the frusto-conically shaped recess of said port so that said fluid path is in fluid communication with said conduit and drawing blood from said blood vessel through said catheter, said hollow interior, said conduit and into said chamber by manipulating said plunger rod;

(e) withdrawing said tip from said port;

(f) providing a needle cannula having a sharp distal end;

(g) connecting said needle cannula to said tip of said syringe barrel;

(h) moving said safety shield to said distal position;

(i) removing said cap from said distal end of said safety shield;

(j) inserting said evacuated receptacle, stopper first, into said safety shield until said sharp distal end of said needle cannula pierces said stopper and enters said cavity of said receptacle;

(k) allowing blood to flow from said syringe chamber through said lumen into said cavity of said receptacle; and (l) removing said receptacle from said safety shield when the desired amount of blood has entered said cavity of said receptacle from said chamber.

14. The method of claim 13 further comprising the additional steps of (m) providing a second evacuated receptacle having a closed end, an opposed open end, a cylindrical side wall therebetween defining a cavity, and a pierceable stopper occluding the open end, the cavity being at subatmospheric pressure;

(n) inserting said second evacuated receptacle, stopper first, into said safety shield until said sharp distal end of said needle cannula pierces said stopper and enters said cavity;

(o) allowing blood to flow from said syringe chamber through said lumen into said cavity of said second evacuated receptacle; and (p) removing said second receptacle from said safety shield when the desired amount of blood has entered said cavity from said chamber.

15. The method of claim 13 wherein the step of providing a syringe assembly includes a syringe without a cap removably connected to the distal end of the safety shield and the step of removing the cap from the distal end of the safety shield is eliminated.

16. The method of claim 13 wherein said syringe barrel includes a collar connected to said distal end of said syringe barrel and inwardly directed projections in said proximal end of said safety shield positioned to cooperate with said collar when said safety shield is in said distal position to lock said shield in said distal position for preventing re-exposure of said sharp distal end of said needle cannula.

17. The method of claim 13 wherein said syringe barrel includes a collar connected to said distal end of said syringe barrel and inwardly directed projections ins aid proximal end of said safety shield positioned to cooperate with said collar for releasably holding said shield when said safety shield is in said distal position.

18. A method of delivering a blood sample to an evacuated receptacle having a closed end, an opposed open end, a cylindrical side wall therebetween defining a cavity, and a pierceable stopper occluding the open end, the cavity being at a subatmospheric pressure, comprising the steps of:
- a) providing a syringe assembly comprising a syringe barrel having an open proximal end, a distal end and a side wall therebetween defining a chamber for retaining fluid, a needle cannula having a sharp distal end and a lumen therethrough connected to said distal end so that said lumen is in fluid communication with said chamber, a cylindrical safety shield having an open distal end and an open proximal end, said safety shield slidably mounted over said syringe barrel for telescoping movement from a proximal position where said needle cannula projects through said open distal end to a distal position where said safety shield protectively surrounds said needle cannula, a piston in fluid-tight slidable engagement inside said barrel, a rigid elongate plunger rod connected to said piston and extending proximally through said open proximal end of said barrel;
- b) piercing a mammalian blood vessel with said sharp distal end of said needle and drawing blood from said blood vessel into said chamber by manipulating said plunger rod;
- c) withdrawing said needle from said blood vessel;
- d) moving said safety shield to said distal needle protecting position;
- e) inserting said evacuated receptacle, stopper first, into said safety shield until said sharp distal end of said needle cannula pierces said stopper and enters said cavity of said receptacle;
- f) allowing blood to flow from said syringe chamber through said lumen into said cavity of said receptacle; and
- g) removing said receptacle from said safety shield when the desired amount of blood has entered said cavity of said receptacle from said chamber.

19. The method of claim 18 wherein said needle cannula is removably connected to said distal end of said syringe barrel.

20. The method of claim 19 including the additional steps immediately after withdrawing said needle from said blood vessel, said steps comprising:
- (c1) disconnecting said needle cannula from said barrel;
- (c2) providing a second needle cannula; and
- (c3) connecting said second needle cannula to said distal end of said syringe barrel.

* * * * *